(12) United States Patent
Carlisle et al.

US008980177B2

(10) Patent No.: US 8,980,177 B2
(45) Date of Patent: *Mar. 17, 2015

(54) FLUIDIC INDICATOR DEVICE

(71) Applicant: Alere Switzerland GmbH, Zug (CH)

(72) Inventors: Stephen John Carlisle, Sherrington (GB); David Tolley, Bedford (GB)

(73) Assignee: Alere Switzerland GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,708

(22) Filed: Jul. 2, 2013

(65) Prior Publication Data

US 2014/0141501 A1    May 22, 2014

Related U.S. Application Data

(63) Continuation of application No. 13/246,104, filed on Sep. 27, 2011, now Pat. No. 8,492,136, which is a continuation of application No. 11/848,175, filed on Aug. 30, 2007, now abandoned.

(30) Foreign Application Priority Data

Aug. 30, 2006    (GB) ...................................... 0617035

(51) Int. Cl.
| | | |
|---|---|---|
| *G01N 31/00* | (2006.01) | |
| *G01N 33/53* | (2006.01) | |
| *G01N 33/558* | (2006.01) | |
| *B01L 3/00* | (2006.01) | |
| *G01N 33/543* | (2006.01) | |
| *G01N 33/76* | (2006.01) | |

(52) U.S. Cl.
CPC ............ *G01N 33/558* (2013.01); *B01L 3/5023* (2013.01); *B01L 3/5027* (2013.01); *G01N 33/54366* (2013.01); *G01N 33/76* (2013.01); *B01L 3/502723* (2013.01); *B01L 3/502753* (2013.01); *B01L 2200/0621* (2013.01); *B01L 2200/148* (2013.01); *B01L 2300/025* (2013.01); *B01L 2300/0681* (2013.01); *B01L 2300/0816* (2013.01); *B01L 2300/0864* (2013.01); *B01L 2400/0406* (2013.01); *G01N 2333/59* (2013.01); *Y10S 436/807* (2013.01)
USPC ............ 422/50; 422/430; 435/7.1; 435/7.21; 435/286.5; 435/287.1; 435/287.2; 436/164; 436/165; 436/501; 436/518; 436/807

(58) Field of Classification Search
CPC .................. B01L 2200/0621; B01L 2200/148; B01L 2400/0406; B01L 3/5023; G01N 2333/59; G01N 33/54366

See application file for complete search history.

(56) References Cited

U.S. PATENT DOCUMENTS

| | | | |
|---|---|---|---|
| 4,963,498 A | | 10/1990 | Hillman et al. |
| 5,198,193 A | * | 3/1993 | Bunce et al. ................... 422/501 |
| 5,275,785 A | * | 1/1994 | May et al. ...................... 422/408 |
| 6,096,509 A | | 8/2000 | Okun et al. |
| 6,637,463 B1 | | 10/2003 | Lei et al. |
| 6,660,141 B1 | * | 12/2003 | Minter et al. .................. 204/400 |
| 6,755,211 B1 | | 6/2004 | O'Connor et al. |
| 8,492,136 B2 | * | 7/2013 | Carlisle et al. ............. 435/287.1 |
| 2001/0046453 A1 | | 11/2001 | Weigl et al. |
| 2002/0119482 A1 | | 8/2002 | Nelson et al. |
| 2003/0041652 A1 | | 3/2003 | Spaid et al. |
| 2003/0185713 A1 | | 10/2003 | Leonard et al. |
| 2005/0087122 A1 | | 4/2005 | Ismagliov et al. |
| 2006/0018790 A1 | | 1/2006 | Naka et al. |
| 2006/0286000 A1 | | 12/2006 | Sundberg et al. |
| 2009/0317793 A1 | | 12/2009 | Jonsmann et al. |

FOREIGN PATENT DOCUMENTS

| | | |
|---|---|---|
| EP | 291194 A1 | 11/1988 |
| EP | 456699 A1 | 11/1991 |
| EP | 0974840 A2 | 1/2000 |
| WO | WO-93/22053 A1 | 11/1993 |
| WO | WO-2004/083859 A1 | 9/2004 |

* cited by examiner

*Primary Examiner* — Lisa Cook

(74) *Attorney, Agent, or Firm* — Foley Hoag LLP

(57) ABSTRACT

Disclosed is a fluidic assay device for assaying at least one property of a liquid sample, the device comprising:
(i) a liquid sample application region;
(ii) at least one test flow path in liquid flow communication with the sample application region;
(iii) a reference flow path in liquid flow communication with the sample application region; and
(iv) a junction region, at which the test flow path and the reference flow path contact one another, the junction region typically comprising an outlet, conduit, chamber or other portion which permits the onward flow of liquid;
wherein a liquid flowing along the reference flow path, upon reaching the junction region, has the effect of preventing the flow of liquid along the test flow path.

The invention relates to a fluidic device for the passage of a liquid. It also relates to an assay device suitable for measurement of the amount and/or presence of an analyte in, or property of, a fluid sample.

12 Claims, 1 Drawing Sheet

FLUIDIC INDICATOR DEVICE

This application is a continuation of U.S. application Ser. No. 13/246,104 filed Sep. 27, 2011 and issued as U.S. Pat. No. 8,492,136, which is a continuation of U.S. application Ser. No. 11/848,175 having a filing date of Aug. 30, 2007, which claims priority to GB 0617035, filed Aug. 30, 2006. The entire contents of each of these applications are hereby incorporated by reference.

BACKGROUND

A problem associated with non-digital assay devices, especially pregnancy-testing devices and/or home-use assay devices, is that they provide an assay result as a signal of variable strength, which can require a degree of interpretation. This leaves the assay result open to misinterpretation, especially where the user or reader of the assay device has a preferred assay result in mind. In the case of some testing devices however, such as a pregnancy-testing device, it is preferred to configure the device such that no interpretation is required and the assay result is provided as one of two alternatives (i.e. pregnant or not pregnant). This may be described as a "binary outcome" device. This provides an unequivocal result which removes the need for interpretation by the user, which is undesirable. Current assay devices or assay device readers incorporate complicated optical and electronic components to read a variable strength signal and then provide a binary outcome via an electronic (e.g. LCD or LED) display.

SUMMARY

Provided are binary outcome assay devices which are far simpler to produce than existing optical/electronic binary outcome assay devices.

Further objectives and advantages of the present invention will become apparent as the description proceeds. To gain a full appreciation of the scope of the present invention, it will be further recognized that various aspects of the present invention can be combined to make desirable embodiments of the invention.

DETAILED DESCRIPTION

Figure 1:
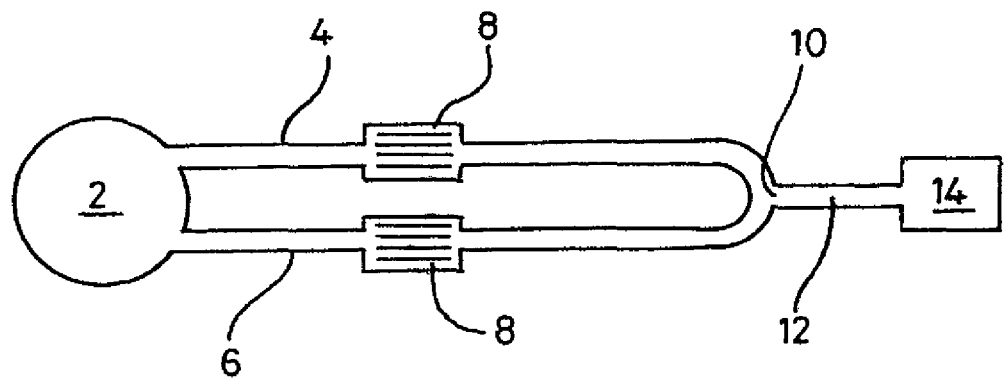
FIG. 1 shows a device according to Example 1.

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The singular forms "a", "an", and "the" include plural references unless the context clearly dictates otherwise.

The terms "comprise" and "comprising" is used in the inclusive, open sense, meaning that additional elements may be included.

The term "sample" refers to any sample potentially containing an analyte. For example, a sample may be a bodily fluid such as blood, urine, mucous or saliva, or a respiratory sample, such as a nasopharyngeal wash or aspirate, nasal swab, nasopharyngeal swab, nasal wash, throat swab, transtracheal aspirate, bronchoalveolar lavage, elution buffer used to wash a respiratory sample, etc.

For the avoidance of doubt it is hereby expressly stated that any features described herein as "preferred," "advantageous," "desirable," "convenient," "typical" or the like may be present in the invention in isolation or in combination with any other feature so described, unless the context dictates otherwise.

Provided in one embodiment is a fluidic assay device for assaying at least one property of a liquid sample, the device comprising:

(i) a liquid sample application region;
(ii) at least one test flow path in liquid flow communication with the sample application region;
(iii) a reference path in liquid flow communication with the sample application region; and
(iv) a junction region, at which the test flow path and the reference flow path contact one another, the junction region typically comprising an outlet, conduit, chamber or other portion which permits the onward flow of liquid; wherein a liquid flowing along the reference flow path, upon reaching the junction region, has the effect of preventing the flow of liquid along the test flow path.

In the event that liquid flowing along the test flow path reaches the junction region before liquid from the reference flow path it is possible, at least in some embodiments, that the flow of liquid along the reference flow path may be prevented. Prevention of the flow of liquid along the reference or test flow path is not necessarily permanent: it is sufficient for the flow of liquid to be prevented within the timescale in which the assay is performed and read.

The test flow path and/or the reference flow path may comprise or consist of a microfluidic channel, a porous carrier, or a combination of the two. Preferred porous carriers include nitrocellulose and filter paper. The microfluidic channel is preferably of capillary dimensions such that a typical sample liquid is able to flow along the channel by capillary flow. Preferably the test and/or reference flow paths comprise or consist of channels having at least a portion with a capillary dimension.

Typical microfluidic channels have an internal cross-sectional dimension of between about 0.1 and about 500 μm, more typically between about 1 and about 100 μm. The microfluidic channels may be formed from synthetic plastics materials such as polycarbonate, epoxy resin etc., glass or metal. The channels may be formed by etching, casting, moulding etc. using conventional techniques.

Typically, but not necessarily, the property of the liquid sample which is assayed comprises the presence and/or amount of an analyte of interest. The analyte of interest may comprise, for example, a steroid, a hormone, a peptide or polypeptide, a carbohydrate, a lipid, a lipoprotein, a polynucleotide, an enzyme, a blood group marker, a disease marker, a diagnostic or prognostic indicator, a cation, an anion, or a molecular complex such as a virus, bacterium, yeast, fungus, spore or eukaryotic cell. In one preferred embodiment the analyte of interest comprises hCG. In another embodiment, the analyte is glucose. A property of a liquid sample that may be determined may be for example a coagulation property of blood or plasma such as prothombin time, partial activated thromboplastin time, thrombin time, and activated clotting time.

The assay device may comprise a control, wherein the control is capable of generating a signal which indicates that sample has been correctly applied to the sample application region and that the assay device is working normally. The control may comprise a control flow path having one or more reagents therein. The reference flow path may also act as a control.

Conveniently the control flow path is such that sample liquid applied to the sample application region will flow along the flow path and typically to an indicator region, either upstream or downstream of the junction region and there generate a signal, typically a visible signal.

The test flow path will generally be substantially similar in character to the reference flow path, but will typically comprise one or more reagents or binding partners which will react with or bind to the analyte of interest. Preferably such reaction or binding event has the effect of altering (typically decreasing) the rate of flow of sample liquid along the test flow path.

The device of the invention can readily be configured to assay for the presence and/or amount of two or more analytes of interest by providing a two or more test flow paths and, optionally, a corresponding number of reference flow paths.

In one embodiment, a separate sample application port or input is provided in the sample application region for each test flow path. In another embodiment the sample application region comprises a common sample application port or input, such that sample liquid applied thereto may flow into two or more flow paths (e.g. two or more test flow paths; or at least a test flow path and a reference flow path). Preferably the device comprises a common sample application port or input which supplies sample liquid to all flow paths present in the device, such that a single sample application step is sufficient to initiate the assay.

The liquid sample may be any suitable liquid, such as water, sewage sample, or an aqueous extract (e.g. an aqueous food or drink sample) or a biological sample e.g. blood, plasma, serum, urine, pus, sweat, saliva, vaginal fluid, or tears. A preferred sample is urine. The liquid sample may be applied to the device 'neat' or may be subjected to a pretreatment step (e.g. including one or more of the following: mixing; agitation; sonication; dilution; incubation; denaturation; or reaction with one or more reagents).

Performance of the assay conveniently comprises reacting or interacting the sample with one or more substances which have the capacity to affect the rate of flow of liquid sample along the test flow path in order to provide an indication or measure of the presence and/or amount of an analyte in, or other property of, the fluid sample. Preferably at least one of the substances will be provided within the assay device, but additionally or alternatively one or more such substances may be mixed with the sample prior to application of the sample to the assay device. Generally, reaction or interaction of the substance(s) with the sample will tend to alter (i.e. increase or decrease) the rate of progress of sample along the test flow path. The substance(s) may be such as to increase the rate of flow of sample liquid along the test flow path if the sample comprises an analyte of interest above a certain minimum detectable concentration. More preferably however the effects of the substance(s) are such as to impede or decrease the rate of flow of sample liquid along the test flow path if the sample comprises the analyte(s) of interest.

In a preferred embodiment the device comprises one or more reagents which react with, or binding partners which bind to, the analyte(s) of interest. Convenient binding partners comprise antibodies or antigen-binding fragments thereof (such as Fab, Fv, scFv, domain antibodies and the like), or multimers of antibodies or antigen-binding fragments thereof.

Other suitable binding partners (depending on the nature of the analyte of interest) may comprise, for example, biotin, streptavidin, complementary polynucleotides (comprising 10 or more, preferably 17 or more, bases of DNA, RNA, PNA, LNA or any combination thereof, optionally including modified or non-naturally occurring bases), and polypeptide receptors or at least portions thereof which retain binding activity for their respective ligand. Receptors include both prokaryotic and eukaryotic polypeptides, numerous examples of which (both full length and truncated) are known.

The reagents or binding partners may be immobilised on the assay device (i.e. remain attached during performance of the assay) or may be releasably attached (i.e. are released from a support during performance of the assay), or may comprise a combination of immobilised and releasably attached reagents or binding partners. For example, in one embodiment, a releasably attached binding partner is provided on a porous carrier located at an upstream portion of the test flow path. In another embodiment an immobilised binding partner is provided in the test flow path. In yet another embodiment a releasably attached binding partner is provided (on a porous carrier or otherwise) at a relatively upstream portion of the test flow path and an immobilised binding partner is provided at a relatively downstream portion of the test flow path. Methods of releasably attaching or of immobilising antibodies and the like on surfaces are well known to those skilled in the art. Conveniently a binding partner is provided within a capillary channel forming part of the test flow path.

The binding partner or reagent may advantageously be labelled. Suitable labels include, but are not limited to, an enzyme, a fluorescent dye, a colored dye and a particle of colloidal gold or other colloidal metal.

According to an embodiment, the presence of analyte may cause an increase in the flow rate of fluid in the test channel. For example binding of an analyte may cause displacement of a species which is conjugated to a detergent, the presence of which in the fluid channel results in an increase in flow rate of the sample.

Conveniently, the binding partner is particulate or comprises a particulate substance. In one embodiment, the binding partner comprises a latex particle or a particle of colloidal gold or other metal. Advantageously, the particle comprises a plurality of binding partner molecules, such that a single particle may simultaneously be bound to a plurality of members of the analyte of interest. Preferably the latex particle is loaded or marked with a direct visual label, such as a colored dye.

In an embodiment, the binding partner or partners are such that an agglutination reaction occurs in the test flow path in the presence of the analyte of interest, which agglutination reaction serves to retard or inhibit the flow of sample liquid along the test flow path. The effect of such retardation or inhibition of flow along the test flow path is that liquid flowing along the reference or control path will reach the junction region first, which in turn blocks the further advance of liquid along the test flow path (as explained below).

In a further embodiment, the test flow path may comprise a reagent such as thromboplastin, or one or more of the various clotting factors, for the determination of a coagulation property of blood or plasma.

According to a further embodiment, the reagent may be Concanavalin A, which is able to react with glucose to cause an increase in viscosity in the fluid sample. The test flow path may comprise a solvent swellable polymer gel which swells in the presence of a particular solvent to cause an increase in viscosity. An example of such is a dextran polymer when the analyte to be detected is water.

The assay device of the present invention can be thought of as using a "race" between the liquid flowing along the test flow path and that flowing along the reference flow path—the first liquid to reach the junction region will win the "race" and block further advance of liquid along the other flow path.

One way of forming the block is to provide a number (one or more) of vents downstream of the junction region. Displacement of the gas (typically air) filling the microfluidic channel of the test and flow paths, via these vents, is necessary to allow liquid to advance along the flow paths. However, once liquid from one of the flow paths has reached the junction, it prevents the venting of gas from the other flow path, forming a gas block (typically an air block), preventing liquid advancing along the blocked flow path. This arrangement is extremely simple, requires no moving parts, and is easy to manufacture.

One or both of the test and reference flow paths may additionally comprise partial barriers to flow, such as constrictions, filters, weirs or the like, which encourage the formation of more total barriers or obstructions in the presence of e.g. an agglutination reaction. Typically such a partial barrier or obstruction is provided in the one or more test flow paths but not in the reference flow path.

The device conveniently comprises at least one indicator region. In one embodiment there is an indicator region located downstream of the junction region. In one embodiment there is an indicator region located upstream of the junction region. In one embodiment there is an indicator region in or on the test flow path and an indicator region in or on the reference flow path, both indicator regions being located between the sample application region and the junction region.

The indicator region comprises a display which displays information about the assay result to a person using the assay device. Typically the assay result is displayed, at least in part, by a color change.

There are a great many ways by which a color change, visible in the indicator region or regions of the device, could be effected.

In one example, there is an indicator region downstream of the junction region. In a simple embodiment, dyes of different colors are provided in the respective test and control flow paths, such that the presence of a dye of a particular color in the indicator region reveals by which route (the test or control flow path) liquid first reached the indicator region. Alternatively, two different enzymes (e.g. horseradish peroxidase and glucose oxidase) could be provided in the indicator region, and a respective substrate for one of the enzymes could be provided in the flow paths which, reacts, in the presence of the relevant enzyme catalyst, to produce a colored product. The color of the product reveals which substrate was introduced into the indicator region (and hence by which flow path liquid first arrived there). In general terms, the indicator region (if located downstream of the junction region) may comprise components of two different signal-generating means which generate detectably different signals, with one or more further components of each signal-generating means being mobilisably disposed upstream, the further component of one signal-generating means being disposed in the test flow path, and the further component of the other signal-generating means being disposed in the reference flow path, the further component being required to contact the other component in the indicator region in order to generate a signal. Which of the two signal-generating means is activated depends on which of the further components reaches the indicator region first, which in turn depends on the relative rates of flow of liquid along the test and reference flow paths.

In one embodiment, the indicator region comprises a pH-sensitive indicator, and the test and reference flow paths each comprise a different pH-affecting agent, e.g., one comprises a buffer at relatively acidic pH and one comprises a buffer at relatively alkaline pH. The flow path by which liquid first reaches the indicator region will therefore determine the pH in the indicator region and hence the color of the indicator.

Embodiments of this general type, with a downstream indicator region, have the advantage that it is not necessary to impede or retard the flow of liquid along the test flow path by a large amount in order for the liquid flowing along the reference flow path to reach the indicator region first—a time differential of as little as 1 or 2 seconds will suffice.

In other embodiments an indicator region is provided, upstream of the junction region, in each of the reference and the test flow paths. In one embodiment, flow of liquid along the reference flow path to a certain point acts to block flow of liquid along the test flow path before the liquid reaches the indicator region on the test flow path, such that a certain assay result is displayed in the indicator region. In some embodiments it may be advantageous to provide an indicator substance, such as a dye, upstream of the indicator region, such that a visible change can be seen if/when liquid reaches the indicator region of the test and/or reference+flow paths.

In some embodiments, the indicator region comprises a microfluidic channel, such as a capillary, which is visible to a user (e.g. through a window or aperture in an otherwise opaque housing). In one embodiment, the indicator region comprises two channels or capillaries, one forming part of the test flow path and one forming part of the reference flow path. In one embodiment, the microfluidic channels or capillaries in the indicator region became filled with a colored liquid during performance of the assay. The color of the liquid may itself indicate the result of the assay. Alternatively, the colored liquid may simply serve to alter the visibility of the channel or capillary. For example, a clear plastics or glass capillary against a clear or white background may not be readily apparent. Introduction of a colored liquid into such a channel or capillary will increase contrast and render the channel or capillary readily visible. Alternatively, if the channel or capillary is initially of high contrast with its background (e.g. a white capillary against a red background), then introduction of a colored liquid into the channel or capillary which is of the same color as the background will reduce the contrast and render the capillary or channel difficult to observe. These all represent different methods of conveying or displaying a visible signal concerning the outcome of the assay.

In some embodiments, the indicator region may comprise one or more channels or capillaries which form one or more words or symbols (such as "PREGNANT", or a plus or minus symbol). In one particular embodiment, in which an assay device in accordance with the invention is provided as a pregnancy test device, one flow path comprises an indicator region in which a channel or capillary forms the word "NOT", and another flow path comprises an indicator region in which a channel or capillary forms the word "PREGNANT". Typically the word "NOT" is formed in the test flow path and the word "PREGNANT" is formed in the reference flow path. If a sample is applied the device which does not contain any hCG (i.e. the subject is not pregnant), liquid is free to flow along both the test and reference flow paths. A colored label e.g. a dye, is transported along both flow paths, making the words "NOT" and "PREGNANT" appear as a message in a display. If a sample comprising hCG is applied to the device, agglutination reagents (e.g. particles of latex coated with anti-hCG antibodies) present in the test flow path reduce the rate of flow so much that liquid in the reference flow path reaches the junction before the liquid in the test flow path can reach the indicator region. This effectively blocks the test flow path, so that the word "NOT" does not become visible and instead the display gives the message "PREGNANT".

In some embodiments it may be preferred to bias the assay device, so as to configure the device such that liquid flowing along the reference flow path will, in the absence of analyte of interest in the sample, reach the junction region slightly before the liquid flowing along the test flow path. This feature applies particularly, but not exclusively, to those embodiments in which an indicator region is provided downstream of the junction region, and in which, for example, the test and reference flow paths are provided with a respective indicator or label. If the times taken for the liquid sample to reach the junction region via the reference flow path and the test flow path were identical, it is at least conceivable that liquid from both flow paths would reach the junction region exactly simultaneously and hence become mixed in the indicator region, which would fail to provide a clear assay result. This can be avoided by making the reference flow path shorter and/or by making the rate of flow along the reference flow path more rapid (e.g. by using a thinner bore capillary).

Provided also are methods of testing for the presence of an analyte of interest in a liquid sample, the method comprising the step of applying the liquid sample to the sample application region of a device in accordance with the first aspect of the invention; and noting or recording the assay result displayed by the device.

Still further provided are methods of making the assay devices provided herein, comprising assembling the necessary elements in an operable relationship.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

FIG. 1 shows a device according to the invention. The device has a sample application region 2 fluidically connected to test flow path 4 and a reference flow path 6, which both comprise a capillary channel. A filter 8 may optionally be provided in one or both of the flow paths. The flow paths converge downstream at a junction region 10 leading to a common channel 12. An indicator region 14 may be provided downstream from the junction region 10.

Liquid sample applied to the device via a sample application port in the sample application region 2 is able to flow respectively along the test and reference flow paths 4, 6 and towards the junction region 10. One or more vents are provided in the common channel 12 and the indicator region 14 to allow air to be displaced from the device by the advance of liquid along the capillaries. However, once one of the fluid fronts has reached the junction region 10, it blocks off the other flow path from the vents, preventing further advance of the liquid along the other flow path. Thus the device only allows for the arrival in the indicator region 14 of fluid flowing along the flow path whose fluid front first reaches the junction region 10. An indication means may be provided in the fluid channels to enable an observer to determine which fluid in the respective channel arrived first. For example dyes of different colors may be provided in each channel such that the fluid sample is able to interact with the dye to produce liquid of a particular color. Thus the presence of a particular colored dye in the indicator region would enable a user to determine which fluid reached the fluid gate first.

Preparation of the Assay Device According to FIG. 1.

A base layer was prepared from agarose coated 200 µm polyester (GelBond, BMA). The appropriate microfluidic features were cut out of a 75 µm thick heat sealing adhesive PE layers using a GraftTeC cutter and the two layers laminated together. Finally a third layer was laminated to the intermediate layer to provide microfluidic channels of 75 µm.

Example 2

Figure 2:
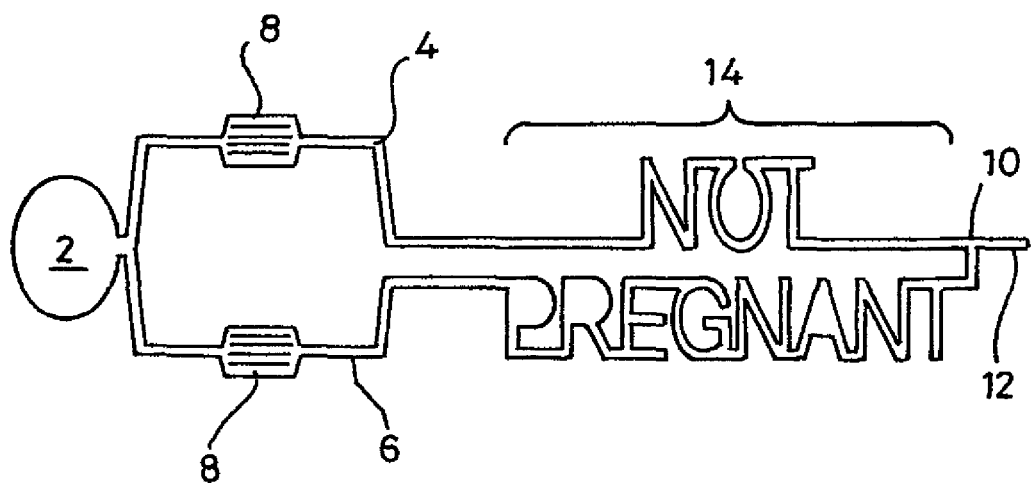
FIG. 2 shows a device according to Example 2.

An alternative embodiment of an assay device in accordance with the invention is illustrated in FIG. 2. Components functionally equivalent to those of the embodiment illustrated in FIG. 1 are denoted by common reference numerals.

As in the previous example, the assay device comprises a sample application port in a common sample application region 2, from which liquid sample can flow into a capillary forming part of the test flow path 4 and a separate capillary forming part of the reference flow path 6. Alternatively each flow path may be provided with a unique, separate sample application region. Those skilled in the art will appreciate that the assay device described in the present examples may be provided with further test flow paths to test for the presence of further analytes of interest. The or each further test flow path can, if desired, be provided with a corresponding reference flow path.

In the embodiment depicted in FIG. 2, each flow path comprises a filter element 8 and an indicator region 14, upstream of a junction region 10.

The filter element 8 comprises one or more binding partners for the analyte of interest, in this instance hCG. In the presence of the analyte of interest the binding partner, particles coated with anti-hCG monoclonal antibody, mediates an agglutination reaction.

Each flow path is also provided with a colored dye which is mobilised by contact, and migrates, with the liquid sample.

The indicator region 14 of each flow path comprises a capillary channel forming the word "NOT" in the test flow path 4 and the word "PREGNANT" in the reference flow path. These capillaries are formed from clear synthetic plastics material and are against a low contrast background (e.g. white or clear synthetic plastics material). Accordingly, prior to performance of the assay, the capillaries are not highly visible.

However, once the assay is initiated, the dye located in the flow paths upstream of the indicator region is mobilised by the advancing liquid sample. If the sample does not contain hCG, liquid is free to flow along both flow paths. The dye-containing liquid thus fills both capillaries, displaying the assay result "NOT PREGNANT". Vents may be provided at several points along the reference flow path to encourage the flow of liquid therealong. In particular these vents may be provided to assist the liquid in filling the indicator region of the reference flow path. Preferably there are no such vents in the test flow path, air being vented from the test flow path capillary 4 only via one or more vents downstream of the junction region 10, in the common channel 12, such that if liquid flowing along the reference flow path 6 reaches the junction region 10 before the liquid front flowing along the test flow path 4, air can no longer be displaced from the test flow path capillary and further advance of the liquid along that channel is prevented.

The rate of flow of liquid along the test and reference flow paths, and/or the length of the respective flow paths, is adjusted such that, in the absence of hCG, liquid flows along both flow paths 4, 6 and fills the respective indicator regions. Typically, in the absence of hCG in the sample, the liquid flowing along the reference flow path will reach the junction region 10 either simultaneously with the liquid flowing along the test flow path or just 1 or 2 seconds in advance thereof.

If however the applied sample comprises hCG, agglutination will take place in the test flow path 4 which substantially retards the advance of liquid along the test flow path capillary towards the indicator region. This allows liquid flowing along the reference flow path to "win the race" to the junction region easily. The liquid flowing along the reference flow path reaches the junction region 10 before the liquid flowing along the test flow path 4 reaches the indicator region. In this instance, the word "NOT" does not become filled with dye and remains indistinct, whilst the word "PREGNANT" becomes highly visible and thus displays the assay result.

Example 3

In order to provide a practical demonstration of the feasibility of the invention 15 μm polystyrene beads (Polysciences) were coated with aminodextran 500,000 RMM, then with NHS-LCLC-Biotin to prepare biotinylated latex beads (NHS=N-hydroxy succinimidyl, LCLC="long chain", i.e. a 12 carbon spacer). Into 50 μl of a 200 μg/ml solution of BSA (to block non-specific binding sites), was added 50 μl of a 5% solution of the 15 μm biotin particles, mixed on a vortex. To the biotinylated particle solution in BSA, 5 μl of streptavidin 1 μm magnetic particle in solution were added solution, while mixing on a vortex to prepare a test fluid. Immediately after preparation, the fluid was added to a microfluidic device as described below.

A reference fluid consisting of BSA buffer was also prepared.

A microfluidic device was prepared having a sample application port provided upstream from a fluid channel of dimensions, 5 mm wide by 3 cm long by 100 μm in height. Provided at a distance of 2 cm along the fluid channel was a filter zone of 5 mm in length comprising channels running parallel to the fluid channel having a 30 μm gap.

Two such devices were prepared and a test solution and reference solution were added respectively to both and the time taken for the fluid front to reach the end of the fluid channel was measured. In this particular example, the test solution took 60 s to reach the end of the channel. In contrast, the reference fluid took just 10 s.

The delay in flow of the test fluid was due to the agglutinated particles becoming stuck in the filter zone. In the case of the reference fluid, no agglutination took place and therefore the fluid is able to flow unimpeded.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.
EP291194
U.S. Pat. No. 4,963,498
EP456699
WO2004/083859

The invention claimed is:

1. A fluidic assay device for assaying at least one property of a liquid sample, the device comprising:
    (i) a liquid sample application region;
    (ii) at least one test flow path comprising a microfluidic channel in liquid flow communication with the sample application region;
    (iii) a reference flow path comprising a microfluidic channel in liquid flow communication with the sample application region; and
    (iv) a junction region, at which the test flow path and the reference flow path converge to a common channel, the junction region comprising an outlet, conduit, chamber or other portion which permits the onward flow of liquid; wherein a liquid flowing along one of the reference flow path or the test flow path, upon reaching the junction region ahead of flow in the other of the test flow path or reference flow path, prevents the flow of liquid along the other flow path.

2. The assay device according to claim 1, wherein the test and/or reference flow paths comprise one or more of the following: a filter; an incubation region; a chamber; a flow restriction; a label; or an indicator.

3. The assay device according to claim 2, wherein the label or indicator is selected from the group consisting of: an enzyme; a fluorescent dye; a colored dye; and a particle of colloidal gold or other metal.

4. The assay device according to claim 1, wherein the test flow path comprises a reagent which reacts with, or a binding partner which binds to, an analyte of interest present in the sample.

5. The assay device according to claim 1, further comprising an indicator region which indicates the result of the assay.

6. The assay device of claim 4 wherein the indicator region comprises nitrocellulose.

7. A method of detecting the presence and/or amount of an analyte of interest in a liquid sample, the method comprising the steps of: applying the liquid sample to the sample application region of an assay device in accordance with claim 1; and noting or recording the assay result.

8. A fluidic assay device for assaying at least one property of a liquid sample, the device comprising:
    (i) a liquid sample application region;
    (ii) at least one test flow path comprising a microfluidic channel in liquid flow communication with the sample application region;
    (iii) a reference flow path comprising a microfluidic channel in liquid flow communication with the sample application region; and (iv) a junction region, at which the test flow path and the reference flow path converge, the junction region comprising an outlet, conduit, chamber or other portion which permits the onward flow of liquid; wherein a liquid flowing along the reference flow path, upon reaching the junction region, prevents the flow of liquid along the test flow path.

9. A fluidic assay device for assaying at least one property of a liquid sample, the device comprising:
(i) a liquid sample application region;
(ii) at least one test flow path comprising a microfluidic channel in liquid flow communication with the sample application region;
(iii) a reference flow path comprising a microfluidic channel in liquid flow communication with the sample application region; and
(iv) a junction region, at which the test flow path and the reference flow path converge, the junction region comprising an outlet, conduit, chamber or other portion which permits the onward flow of liquid; wherein a liquid flowing along the test flow path, upon reaching the junction region, prevents the flow of liquid along the reference flow path.

10. A fluidic assay device for assaying at least one property of a liquid sample, the device comprising:
(i) a liquid sample application region;
(ii) at least one test flow path comprising a microfluidic channel in liquid flow communication with the sample application region;
(iii) a reference flow path comprising a microfluidic channel in liquid flow communication with the sample application region; and
(iv) a junction region, at which the test flow path and the reference flow path converge to a common channel, the junction region comprising an outlet, conduit, chamber or other portion which permits the onward flow of liquid; wherein either the test flow path, the reference flow path or both the test flow path and reference flow path comprise an indicator region.

11. The fluidic assay device of claim 8 wherein the indicator region of either the test flow path, the reference flow path or both the test flow path and reference flow path is upstream of the junction region.

12. The fluidic assay device of claim 8 wherein the indicator region of either the test flow path, the reference flow path or both the test flow path and reference flow path is downstream of the junction region.

\* \* \* \* \*